United States Patent [19]
Goldberger

[11] Patent Number: 5,237,994
[45] Date of Patent: Aug. 24, 1993

[54] INTEGRATED LEAD FRAME PULSE OXIMETRY SENSOR

[75] Inventor: Daniel S. Goldberger, San Francisco, Calif.

[73] Assignee: Square One Technology, Almeda, Calif.

[21] Appl. No.: 667,817

[22] Filed: Mar. 12, 1991

[51] Int. Cl.$^5$ .............................................. A61B 5/00
[52] U.S. Cl. ...................................... 128/633; 356/41
[58] Field of Search ................... 128/633, 664, 665; 356/41

[56] References Cited

U.S. PATENT DOCUMENTS

| | | |
|---|---|---|
| 4,685,464 | 8/1987 | Goldberger et al. |
| 4,700,708 | 10/1987 | New, Jr. et al. ................... 128/633 |
| 4,825,879 | 5/1989 | Tan et al. |
| 4,830,014 | 5/1989 | Goodman et al. |
| 4,834,532 | 5/1989 | Yount |
| 4,865,038 | 9/1989 | Rich et al. ........................... 128/633 |
| 4,964,408 | 10/1990 | Hink et al. ......................... 128/633 |
| 4,974,591 | 12/1990 | Awazu et al. ....................... 128/633 |
| 5,069,213 | 12/1991 | Polczynski |
| 5,094,240 | 3/1992 | Muz .................................... 128/633 |

OTHER PUBLICATIONS

Jonas A. Pologe, "Pulse Oximetry: Technical Aspects of Machine Design".
Stan Gage, "Optoelectronics/Fiber-Optics Applications Manual".
Mark Yelderman, "Pulse Oximetry".
Magnavox Company, "Connectors and Interconnections Handbook, vol. 2, Connector Types".
Mark Yelderman, M.D., et al, "Real Time Oximetry".
Ohmeda ad.

Primary Examiner—Lee S. Cohen
Assistant Examiner—Kevin Pontius
Attorney, Agent, or Firm—Hale and Dorr

[57] ABSTRACT

Disclosed is an integrated lead frame pulse oximetry sensor which includes a thin metal lead frame to which is connected light emitting diodes and a photodiode chip for the purpose of emitting light and detecting light respectively. The thin metal frame is deformable to attach to perfused tissue. The lead frame has a very low mass which diminishes its acceptability to motion induced artifact.

30 Claims, 15 Drawing Sheets (SECTION)

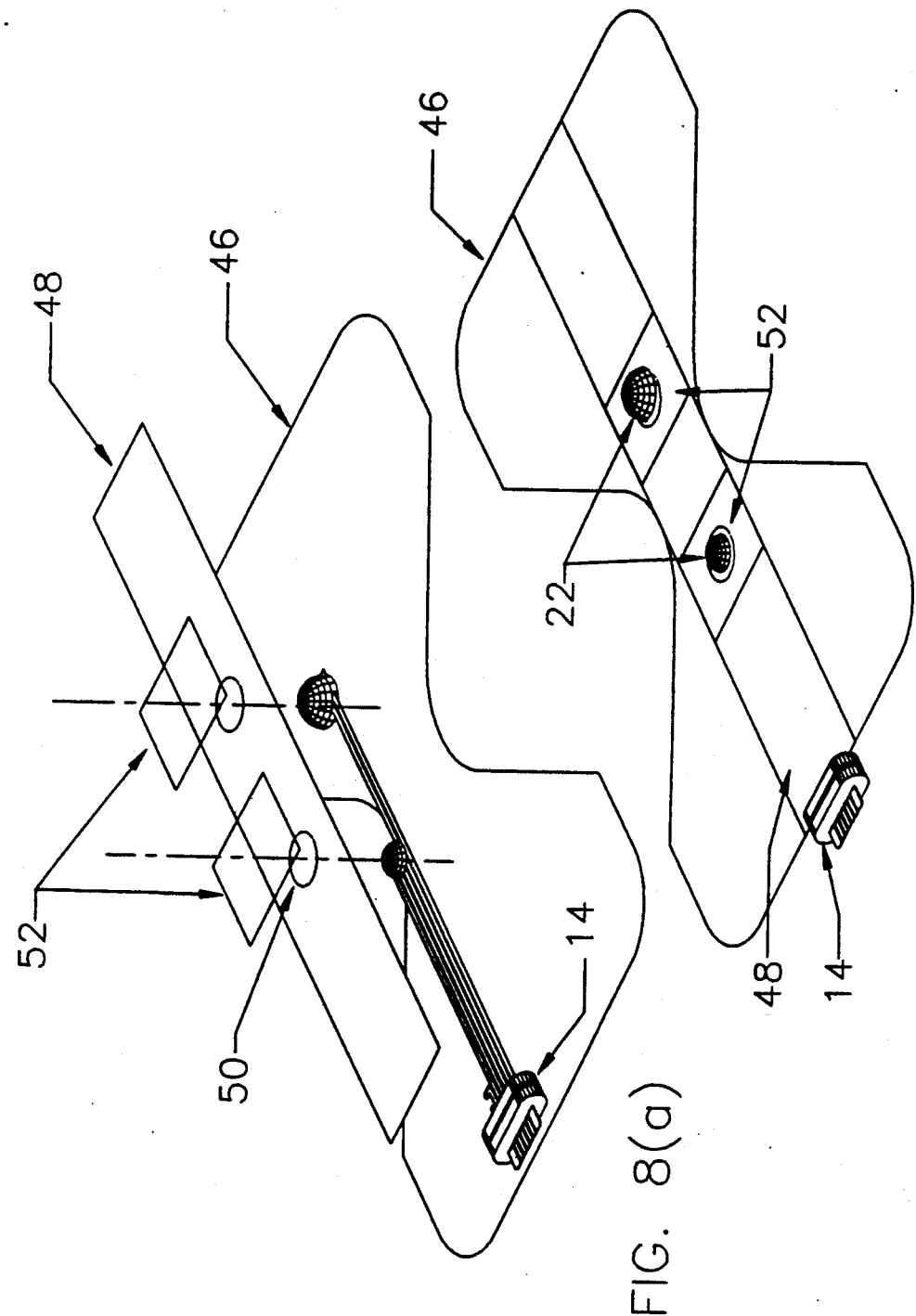

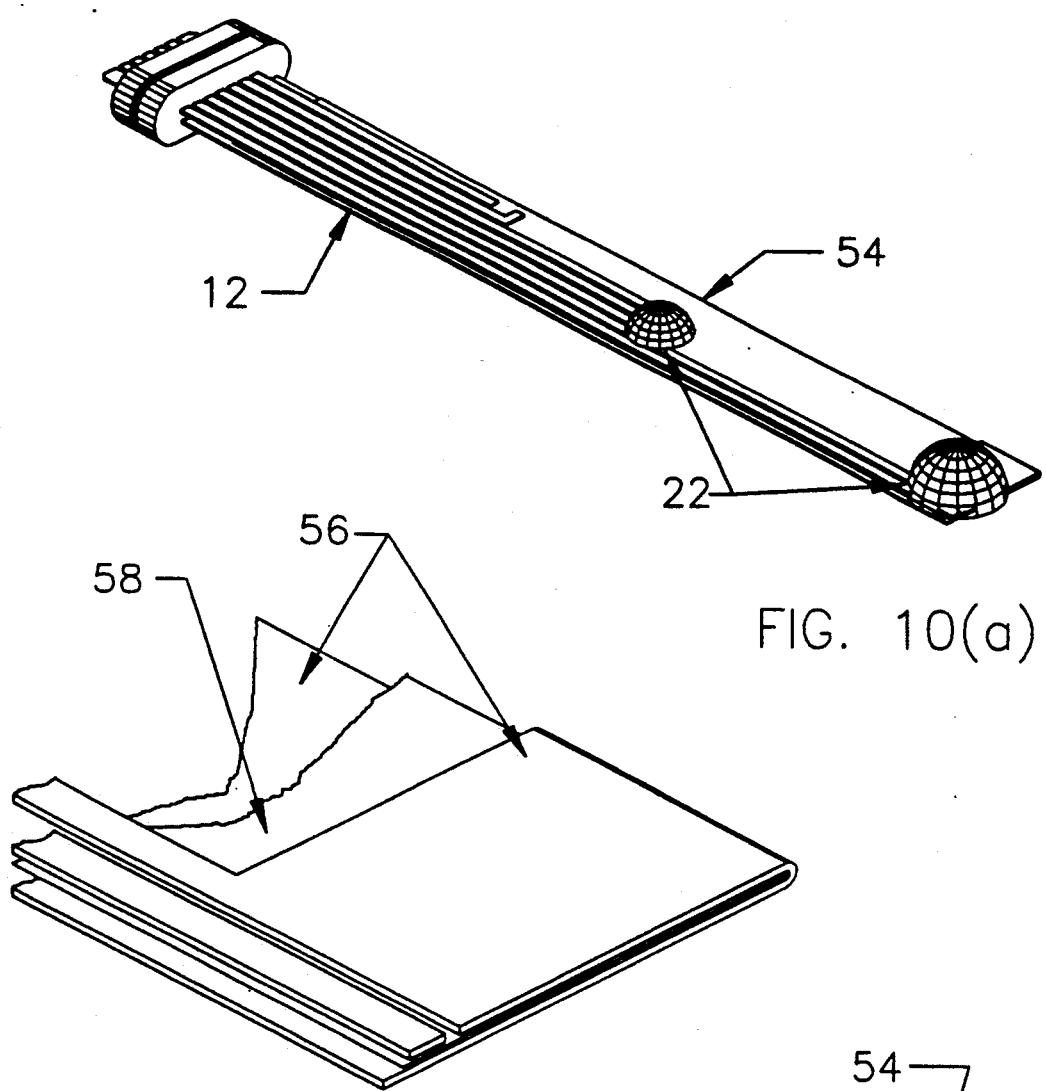
FIG. 10(a)
FIG. 10(b)
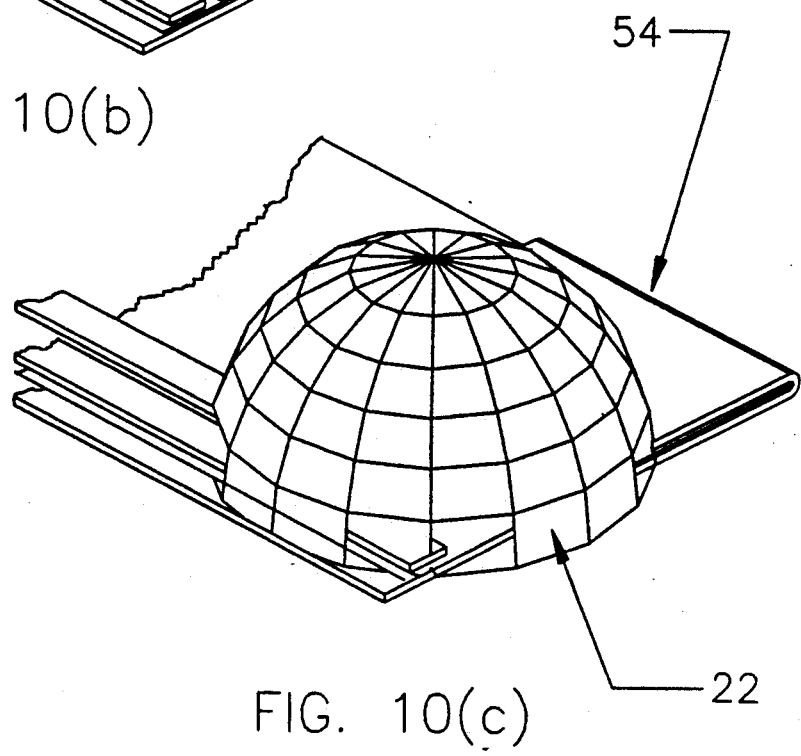
FIG. 10(c)

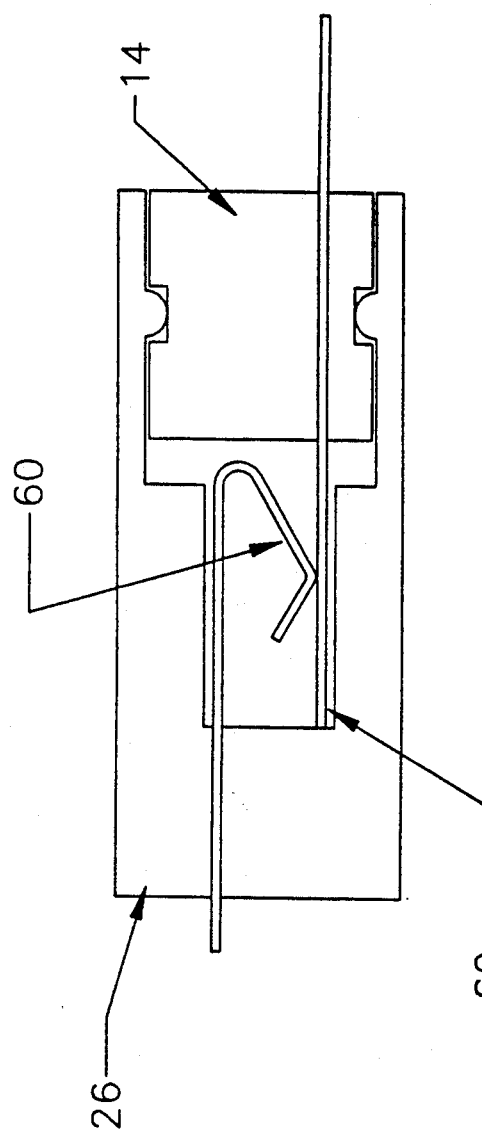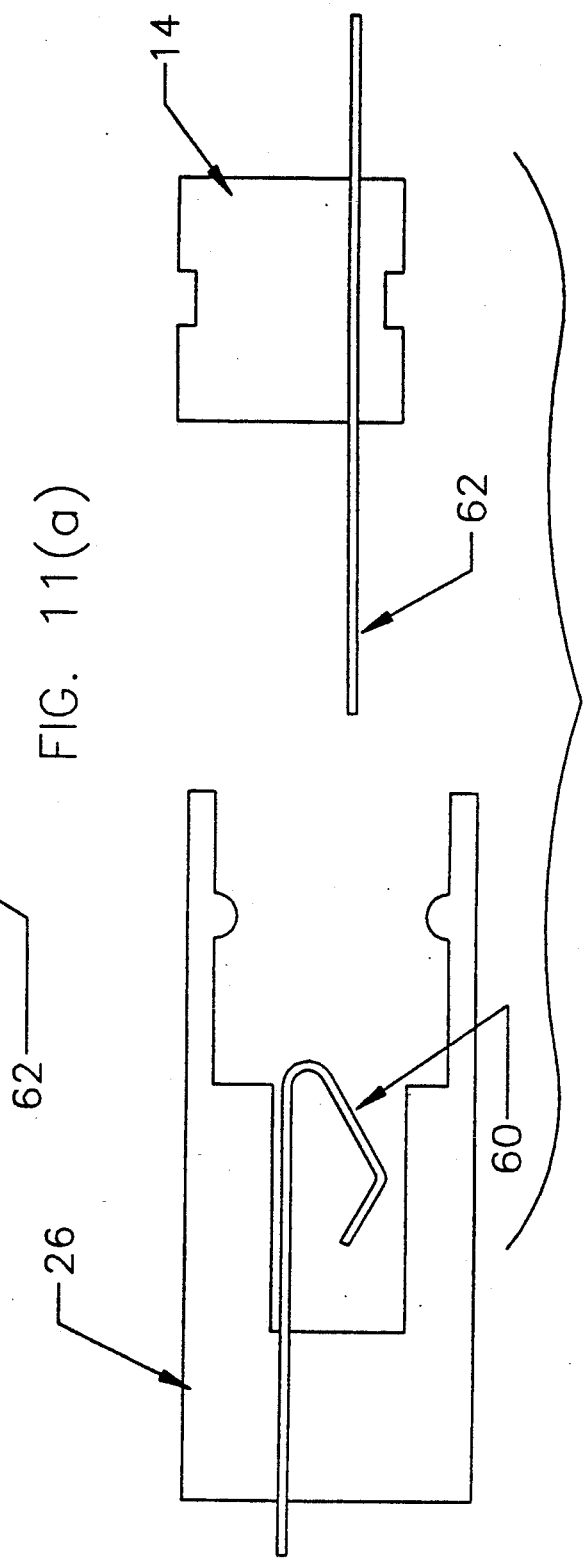

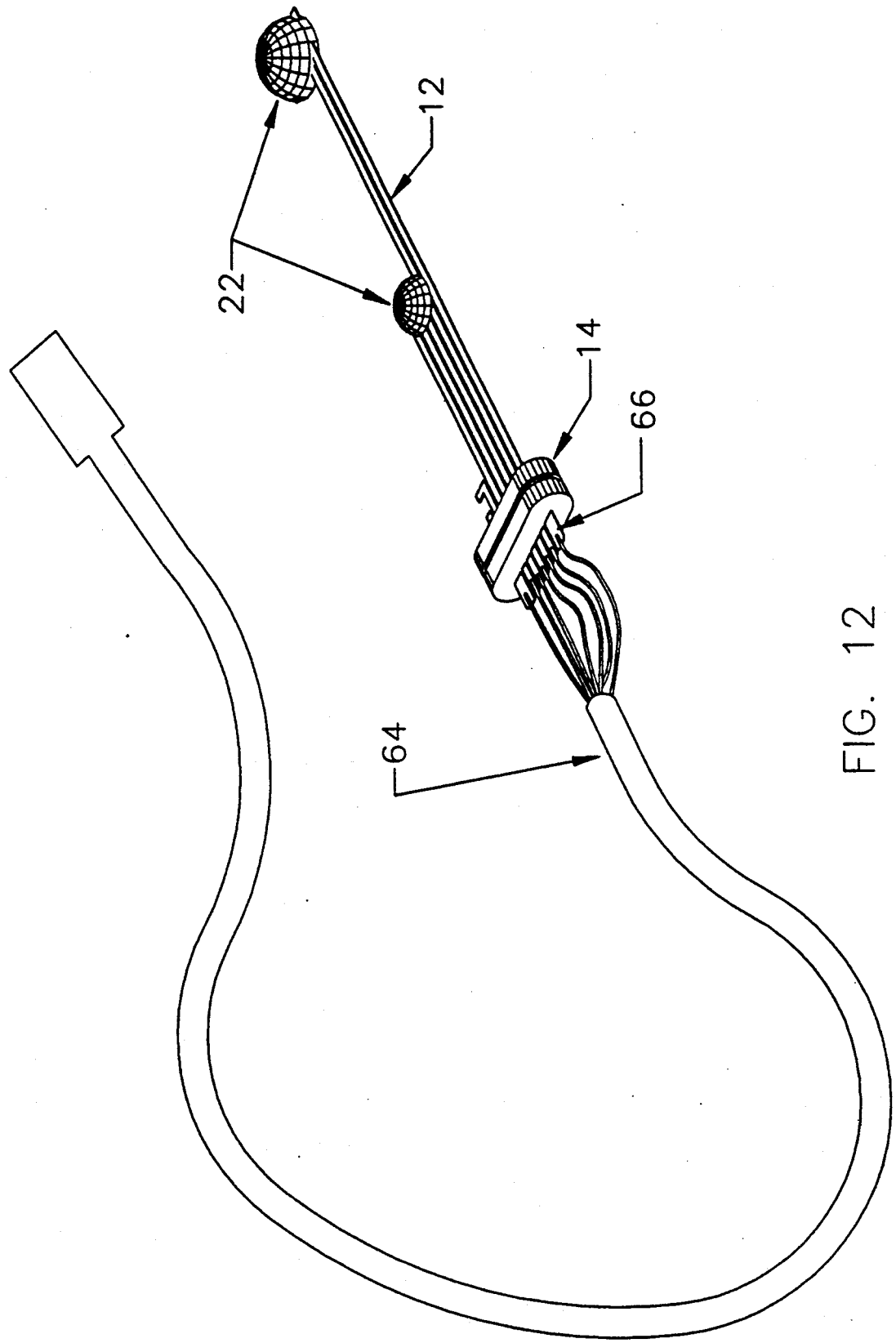

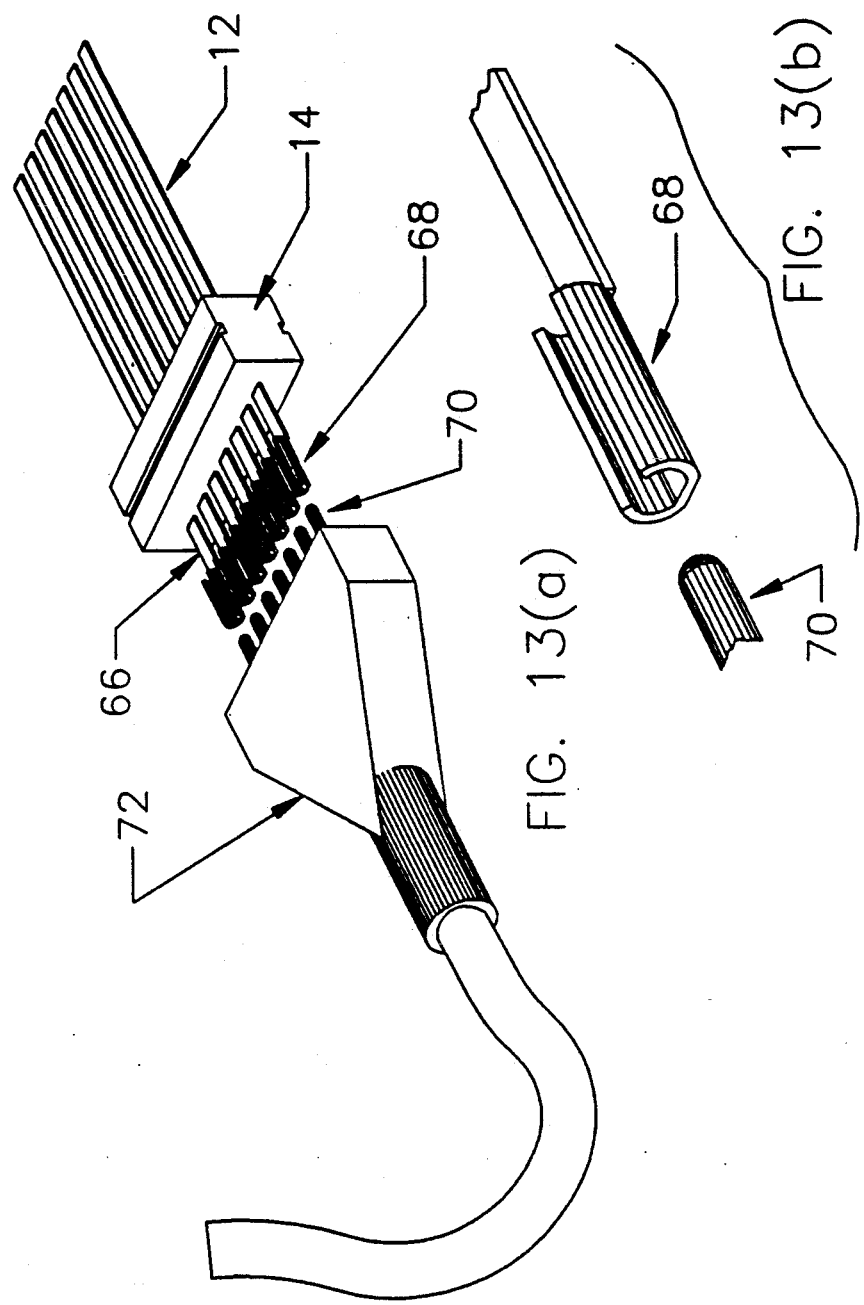

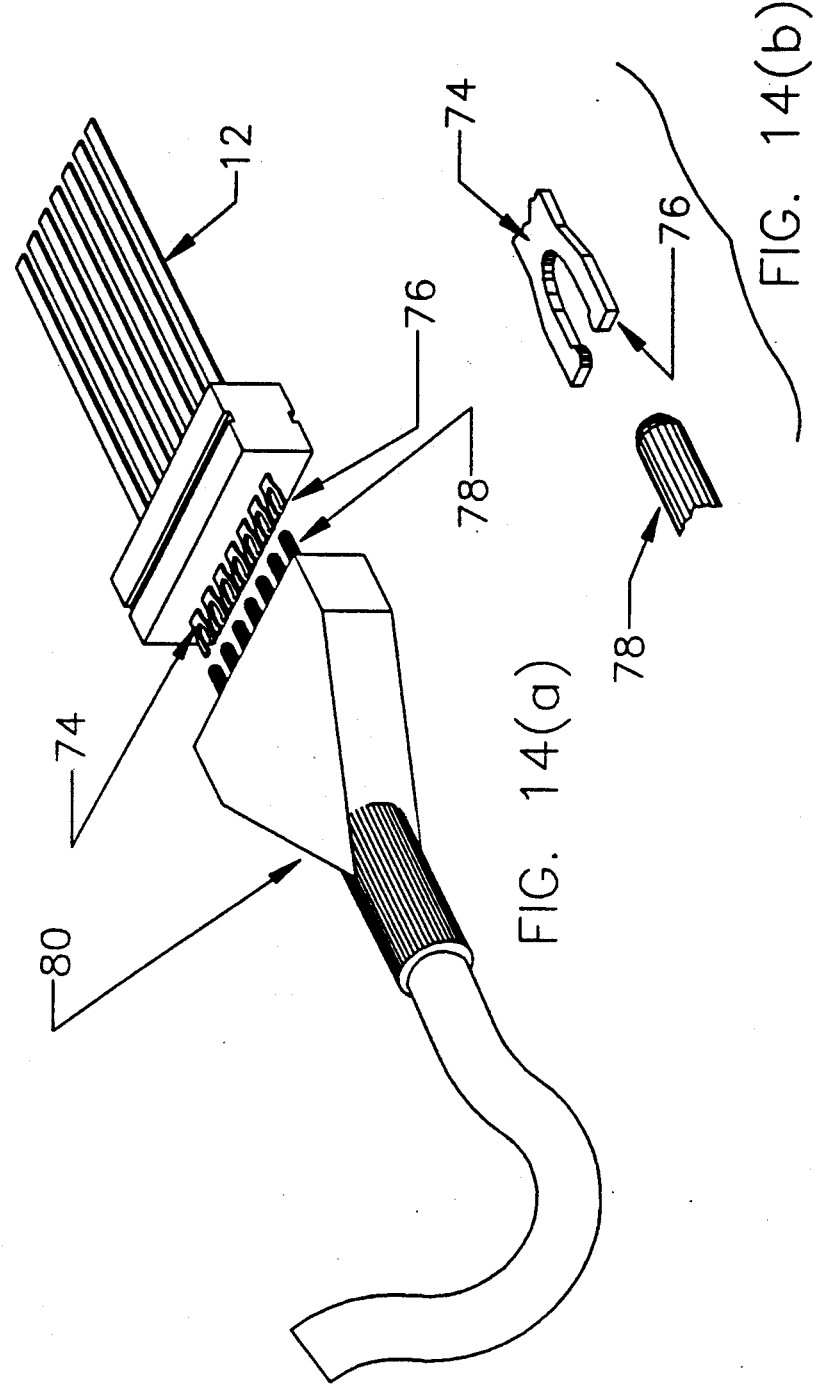

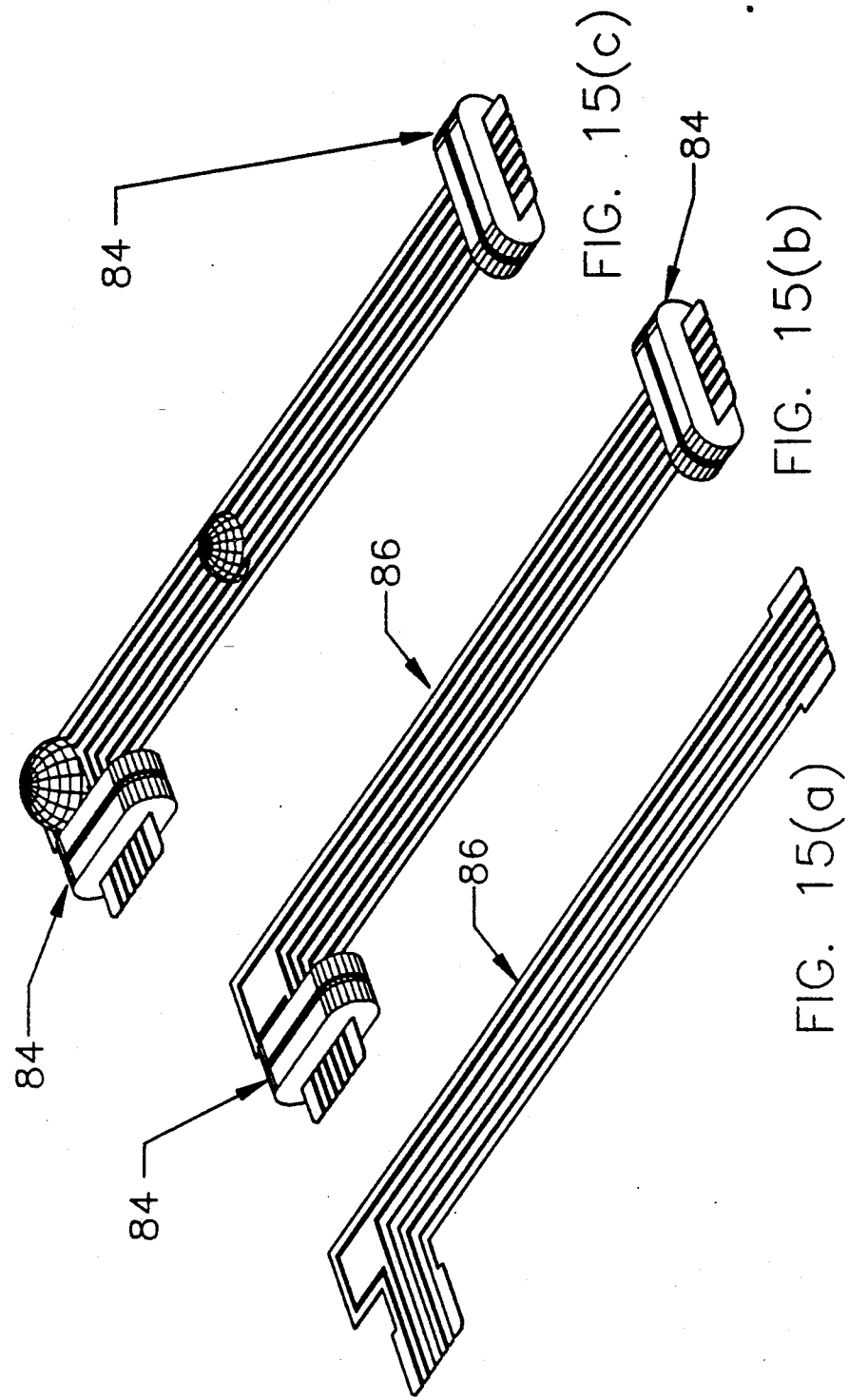

INTEGRATED LEAD FRAME PULSE OXIMETRY SENSOR

BACKGROUND OF THE INVENTION

This invention relates to a pulse oximetry sensor and more particularly to a lead frame for an integrated pulse oximetry sensor.

It is common in medical practice to measure pulse rate and oxygen saturation in blood. Pulse oximetry uses discrete wavelengths of light to measure the optical density of hemoglobin. Pulse oximetry can also distinguish arterial blood from venous blood and tissue.

Pulse oximeters are used extensively in critical care areas of hospitals to monitor a patient's arterial % oxygen saturation ($S_pO_2$) and pulse rate (PR). The pulse oximetry instrument records the absorption of light in perfused tissue at two or more wavelengths. The instrument computes $S_pO_2$ and PR by comparing the time variant and time invarient portions of the light absorption signal. The history and technology of oximetry is well known in the art and it is thoroughly discussed in chapter 16 of *Monitoring in Anesthesia and Critical Care Medicine* which is edited by C. D. Blitt M.D., the teachings of which are incorporated herein by reference.

The preferred site for a pulse oximetry sensor is a finger tip, although other sites are commonly used. The sensor must incorporate light sources, a photodetector, means for mechanically orienting the components relative to the tissue and means for energizing the light sources and returning the optical signals to the pulse oximetry instrument. The sensor must also incorporate means for mechanical attachment to the perfused tissue.

While there are several sensors currently in use, these sensors have several shortcomings. In some cases the sensors have too great a mass and therefore a significant motion artifact is developed when the sensor is in use. Other known sensors conform to the perfused tissue by applying a compressive force and in some cases the compressive force, while sufficient to secure the sensor to the profuse tissue, induces vascular shut down.

It is therefore a principal object of the present invention to provide an integrated lead frame pulse oximetry sensor that can be mechanically attached to perfused tissue yet is of a very low mass.

Another object of the present invention is to provide an integrated lead frame pulse oximetry sensor which can be mechanically attached to perfused tissue without applying compressive forces thereby avoiding vascular shut down.

Still another object of the present invention is to provide an integrated lead frame pulse oximetry sensor which can be manufactured at a cost that is low compared to other known sensors.

SUMMARY OF THE INVENTION

The integrated lead frame pulse oximetry sensor of the present invention includes a thin metal lead frame to which is connected light emitting diodes and a photodiode chip for the purpose of emitting light and detecting light respectively. The thin metal frame is deformable to attach to perfused tissue. The lead frame has a very low mass which diminishes its susceptibility to motion induced artifact.

These and other features and objects of the present invention will be more fully understood from the following detailed description which should be read in light of the accompanying drawings in which corresponding reference numerals refer to corresponding parts throughout the several views.

BRIEF DESCRIPTION OF THE DRAWINGS

FIGS. 8(a)-8(b) are plan views of the lead frame of the present invention used in a butterfly shaped sensor;

FIGS. 10(a)-10(c) are perspective views of an alternate embodiment of the lead frame shown in FIG. 1 which utilizes a grounded shield;

FIGS. 11(a)-11(b) are front sectional views of electrical connection of the connector system incorporated in the lead frame shown in FIG. 1;

FIG. 12 is a perspective view of an alternate embodiment of the integrated lead frame sensor of FIG. 3 in which the cable is permanently attached to the sensor lead frame traces;

FIGS. 13(a)-13(b) are perspective views of another alternate embodiment of the integrated lead frame shown in FIG. 1 which utilizes a pin and socket connector system.

FIGS. 14(a)-14(b) are perspective views of another alternate embodiment of the integrated lead frame shown in FIG. 1 which utilizes a cantilevered "U" socket connector system.

FIGS. 15(a)-15(c) are perspective views of another alternate embodiment of the integrated lead frame shown in FIGS. 1-3 which provides for two different cable attachment points and a variable number of leads.

DETAILED DESCRIPTION OF THE PREFERRED EMBODIMENTS

Figure 1:
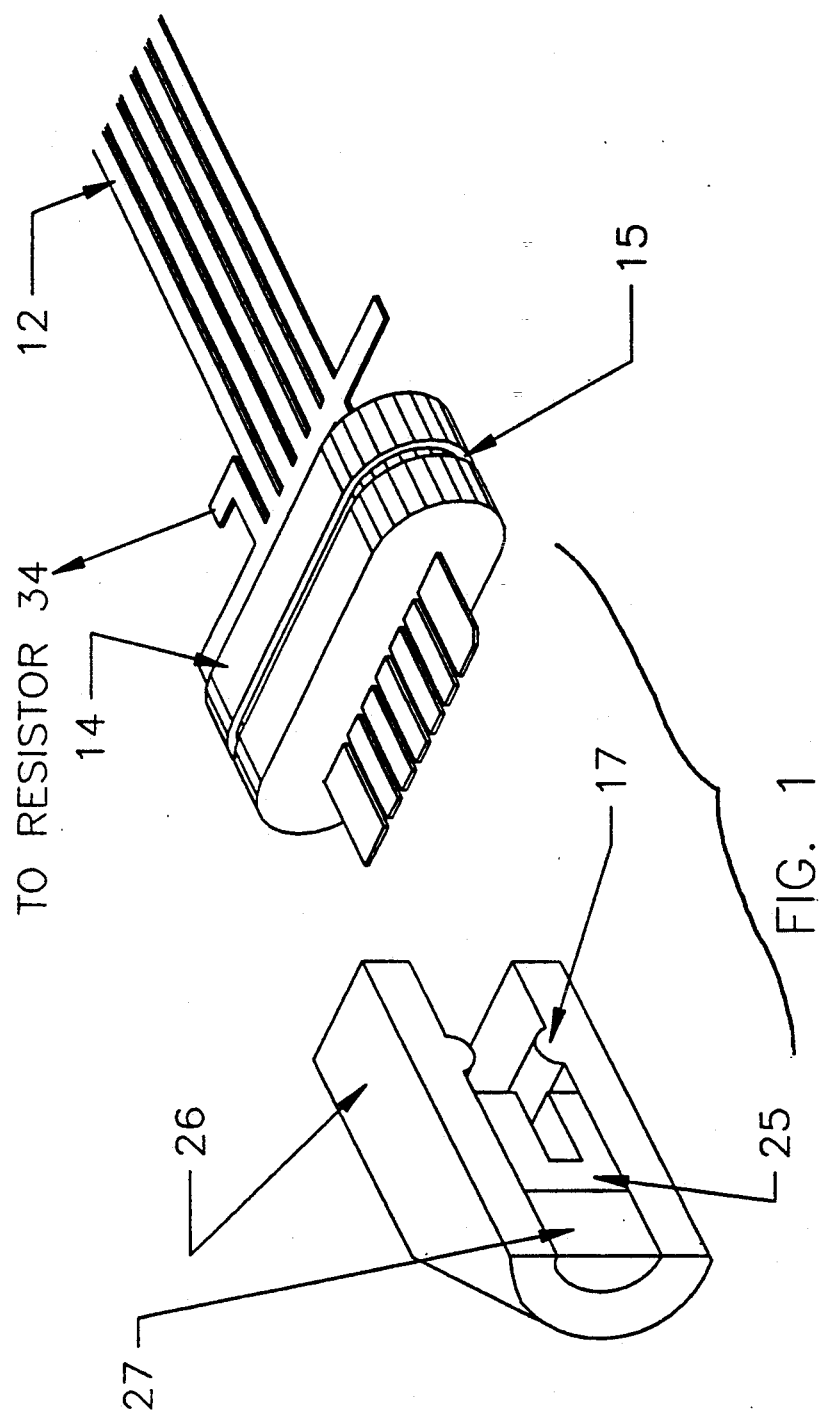
FIG. 1 is a perspective view of a portion of the integrated lead frame sensor of the present invention and an associated female connector.

Referring to FIG. 1 the integrated lead frame 12 for a pulse oximetry sensor of the present invention provides electrical interconnection, mechanical orientation of components, and a means for attachment to perfused tissue.

Figure 2:
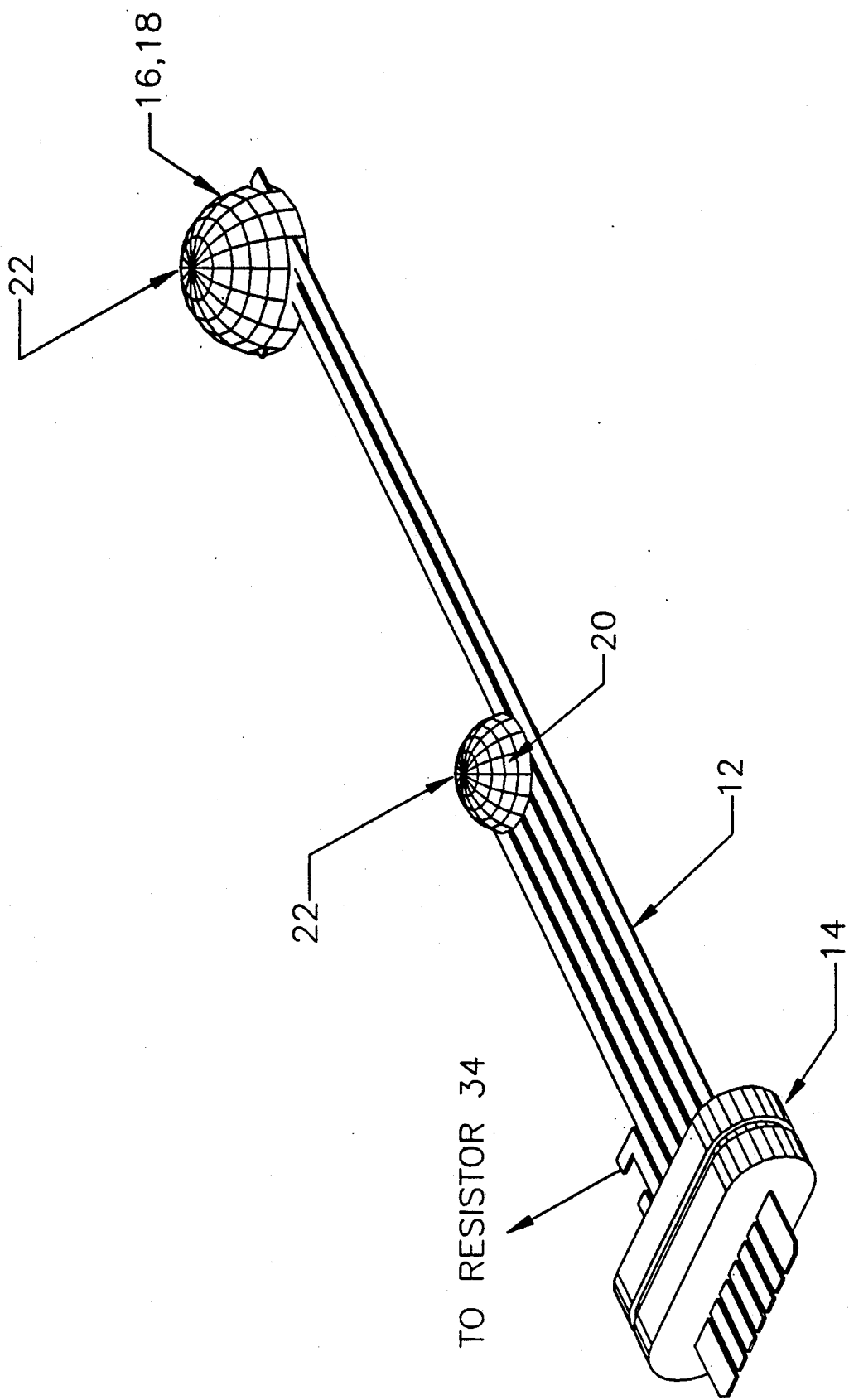
FIG. 2 is a perspective view of the entire integrated lead frame sensor of the present invention.

In a preferred embodiment the lead frame 12 is made from 0.1 mm to 0.3 mm thick steel or copper sheet and seven leads 13 are formed in the frame by stamping or chemical machining. A plastic connector shell 14 is placed near one end of the lead frame 12 and is formed by insert molding. As shown in FIG. 2, red and infrared light emitting diodes 16, 18 ("LEDs") and a photodiode chip 20 are attached directly to the lead frame 12. In a preferred embodiment the attachment is made with silver filled epoxy and electrical connections are made with gold ball or wedge bonding. The LED's and photodiode are subsequently encapsulated in plastic lenses 22 by transfer molding or casting. The assembly is subsequently sealed in an envelope of thin, transparent plastic film (not shown) to provide electrical insulation. The insulating film may or may not be coated with pressure sensitive adhesive and it may or may not have opaque sections between transparent windows.

Figure 3:
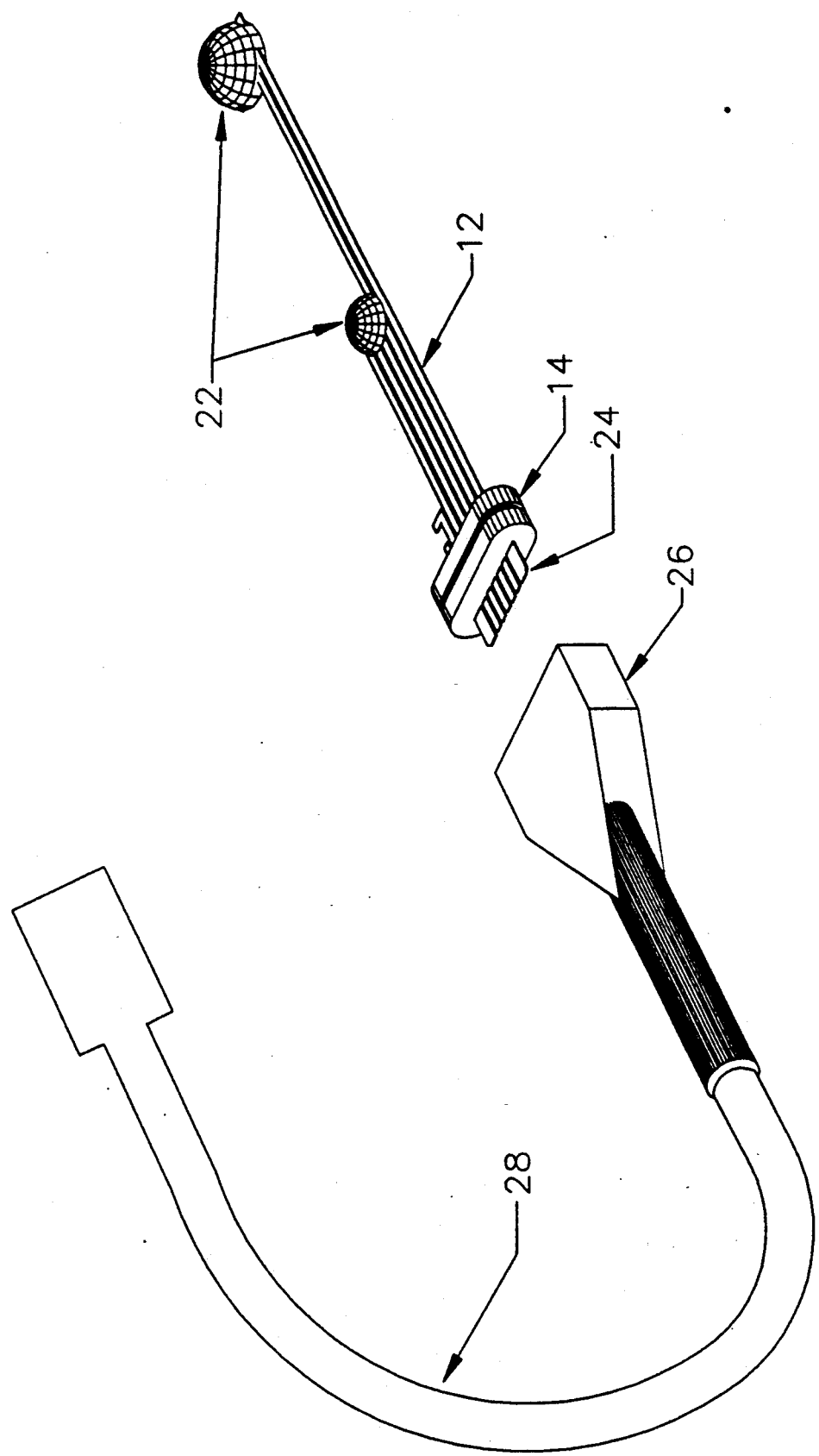
FIG. 3 is a perspective view of entire integrated lead frame sensor of the present invention together with a reusable cable connector.
Figure 4:
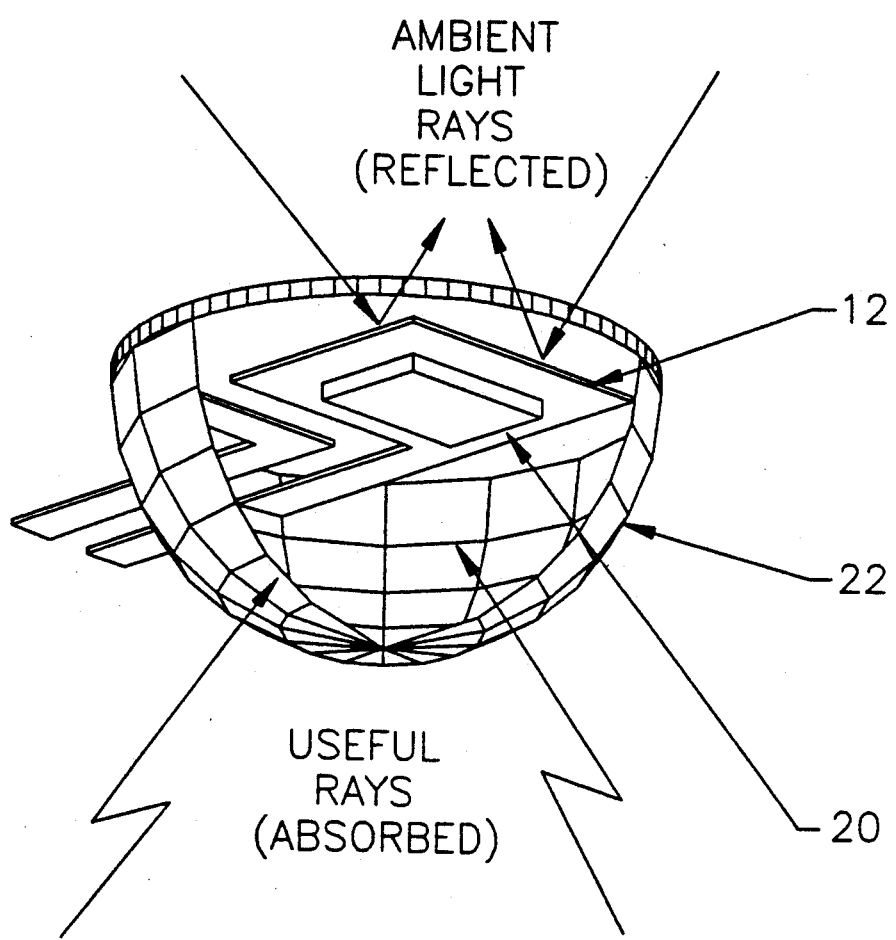
FIG. 4 is a perspective view of the photodiode as connected to the integrated lead frame sensor shown in FIGS. 1-3.
Figure 5:
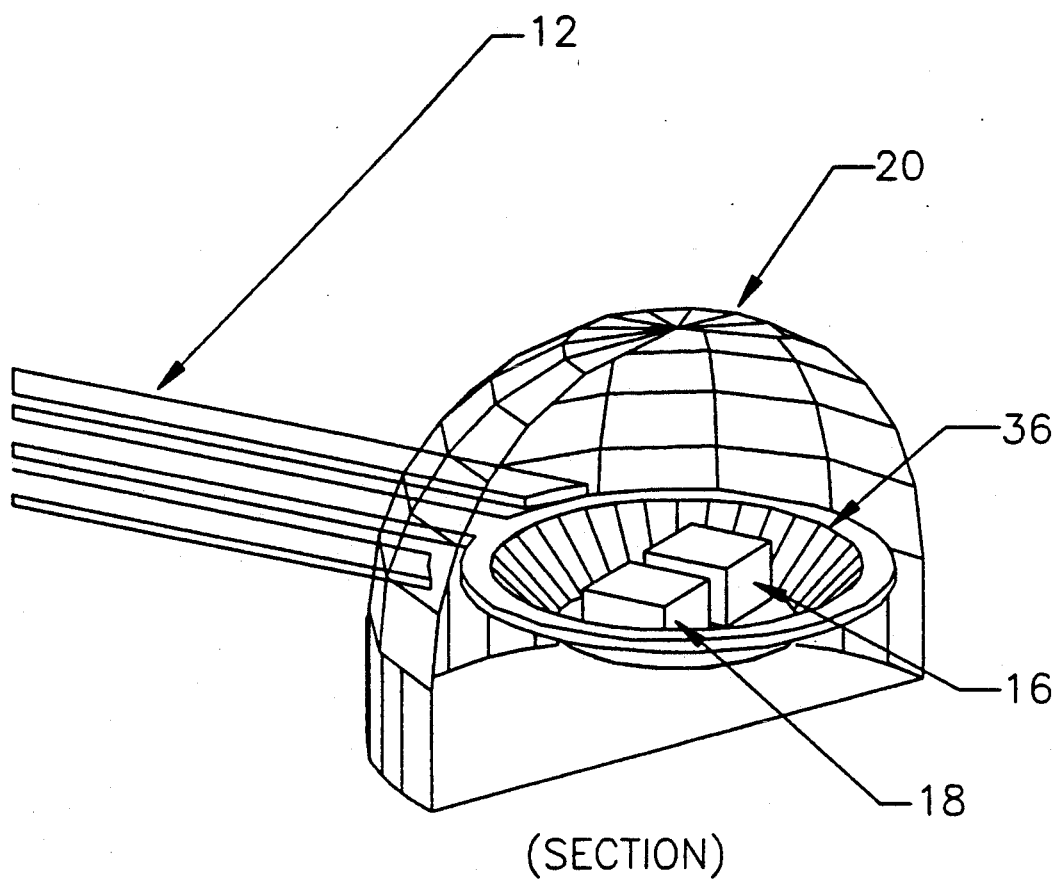
FIG. 5 is a perspective view, partly in section, of the light emitting diodes as connected to the integrated lead frame sensor shown in FIGS. 1-3.

As shown in FIGS. 1 and 3, the male electrical connector 24 formed by the lead frame 12 and the insert molded connector shell 14 mates with a female connector 26 on the end of a cable pigtail 28. In a preferred embodiment the insert molded connector shell 14 includes a groove 15 which mates with a projection 17 in the female connector 26 in order to retain a snug connection and to provide a moisture seal. The female connector 26 also includes a silicon rubber connector boot 25 and a 7 conductor cable 27.

In a preferred embodiment, the device to which the pulse oximetry sensor of the present invention is connected is a pulse oximeter monitor. Examples of suitable monitors are those manufactured by Nelcor Incorporated of Hayward, Calif. under the designation N-100 or N-200 or those monitored by Ohmeda (a division of the BOC Group, Inc.) of Louisville, Colo. under the designation 3740.

In one preferred embodiment the lead frame is fabricated from 0.005 inch think copper alloy C194 with 0.00005 inch thick nickel plating overall and with 0.000075 inch thick selective gold plating on wire bonding pads only. The lead frame may also be plated with gold, silver or palladium.

A suitable red light emitting diode 16 is that sold by Showa Denko of San Mateo, Calif. as part number ARH-35. This LED has a typical light output of 9 candellas at a wavelength of 655 nanometers. A suitable infrared light emitting diode 10 is that manufactured by Showa Denko of San Mateo, Calif. under part number IR-35 which has a typical light output of 0.9 milliwatts at a wavelength of 940 nanometers.

A suitable silicon photodiode 20 can be obtained from Silicon Detector Corporation of Camarillo, Calif., which sells the photodiode as part number 150-3842. This photodiode has a typical response of 0.5 amp/watt and a wavelength of 900 nanometers. The photodiode has an active area of 0.56 inches×0.56 inches.

The lead frame 12 provides means for electrical connection and mechanical orientation of the light sources 16, 18 and the photodetector 20 and eliminates the need for additional substrate components. The metal lead frame can be formed, plated or polished as appropriate to optimize light emission or detection. The lead frame also provides means for holding the photoactive components while a precision lens is molded to encapsulate them. The design of such precision lenses is well known in the art as described in *Optoelectronics/Fiber-Optics Applications Manual* which is prepared by the application engineering staff of Hewlett-Packard Optoelectronics Division and is published by McGraw-Hill Book Company and the teachings of which are incorporated herein by reference. In a preferred embodiment, the precision lens is molded out of a transparent, electrically insulating epoxy manufactured by Ablestick Laboratories of Gardena, Calif. under the designation Ablebond ® 342-3, which enables the lens to increase the amount of light coupled into and out of the perfused tissue. The lens may also be tinted to provide additional shielding from ambient light.

The self-supporting lead frame 12 deforms plastically as it is bent to conform to a finger tip so that it will accurately retain its shape after it is applied to the finger tip. The material and thickness of the lead frame can be chosen to optimize this behavior. The sensor can be further retained by pressure sensitive adhesives or bandages so that it will not tend to spring open. The low mass and thin construction of the integrated lead frame of the present invention act to diminish the sensor's susceptibility to motion induced artifact thereby enabling the lead frame to be used with a wide variety of sensor designs.

In a preferred embodiment a calibration resistor 34 is mounted on the lead frame 12 so that the sensor incorporating the lead frame can be used with a wide variety of pulse oximetry instruments. The resistor 34 has a coded known resistance, and it enables the pulse oximetry instruments to calculate the coefficient of extinction of the wavelengths of the LEDs 16, 18. The pulse oximetry instrument is programmed at the factory to calculate the coefficient of extinction of any LEDs which may be encountered in a series of sensors. From the coefficients of extinction, the pulse rate and degree of arterial oxygen saturation is computed and displayed by the pulse oximetry instrument. A suitable calibration resistor system is described in U.S. Pat. No. 4,700,708, the teachings of which are incorporated herein by reference.

Figure 6:
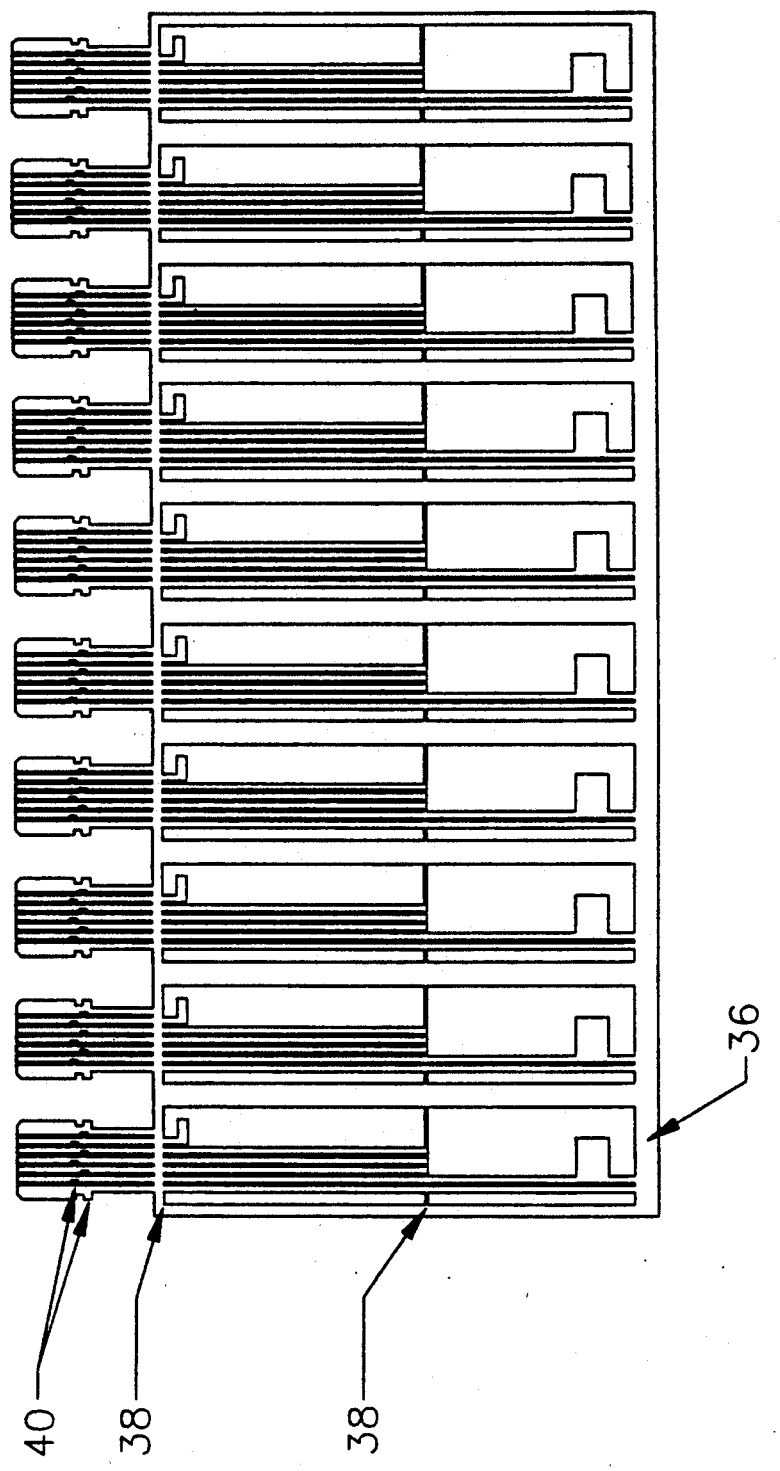
FIG. 6 is a top plan view of a panel of lead frames prior to any processing steps being performed on the lead frames.

The integrated lead frame sensor described above for use in conjunction with pulse oximeters lends itself to manufacture by conventional semiconductor packaging techniques. As such the integrated lead frame sensor can be fabricated by highly automated equipment at low cost. The manufacturing cost is further reduced by eliminating intermediate substrates and interconnections. Referring to FIG. 6, the lead frames 12 are generally manufactured as a panel of lead frames which must then be separated. The lead frames can then be supplied as a single unit or in a panel of many elements. When a panel is supplied subsequent process steps can be performed on several parts simultaneously, thereby reducing the costs of the finished sensor. In addition, the external frame 36 can include features which permit automatic parts handling for additional efficiency. Retention elements 40 may also be included to create an interlocking geometry when the connector housing 26 is molded in place.

Figure 7A:
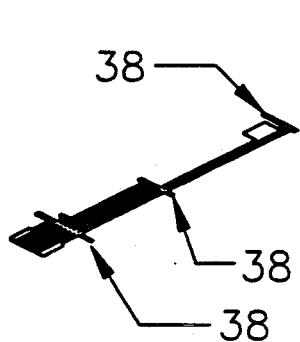
FIGS. 7(a)-7(e) are perspective views of the lead frame of the present invention in various stages of assembly.
Figure 7B:
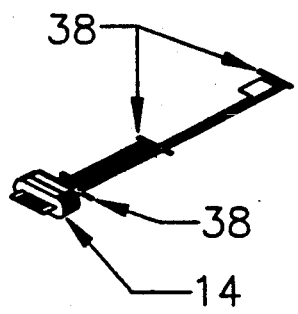
Figure 7C:
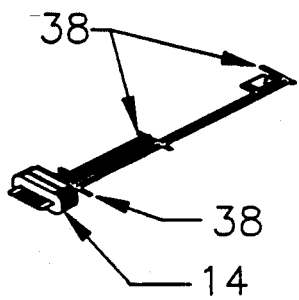
Figure 7D:
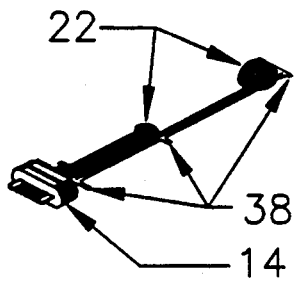
Figure 7E:
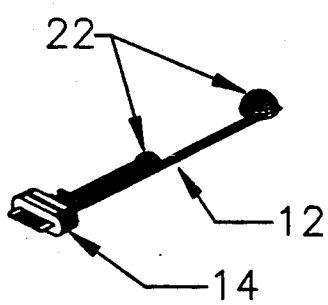

Referring to FIGS. 7(a)-7(e), the manufacturing steps for the lead frame will now be described. When the lead frame 12 is produced as part of a panel of lead frames, individual lead frames must be cut from the panel so that only the lead frame element 12 remains. As a result, the external frame element 36 must be cut from the lead frame 12. Next, as shown in FIG. 7(b) the plastic connector shell 14 is molded onto the connector housing 12, and then the LEDs 16, 18 and the photodiode 20 are wire bonded to the lead frame 12 as shown in FIG. 7(c). In FIG. 7(d) the plastic lenses which provide the transparent encapsulation are placed over the LEDs 16, 18 and the photodiode 20. Finally, the tie bars 38 are removed from the lead frame element.

After the lead frame 12 is assembled, it is then mounted in a particular type of sensor which can take on a variety of shapes for use with bodily parts such as hands, feet, fingers, toes, ears, etc. Referring to FIGS. 8(a)-8(b), a butterfly sensor is shown which is designed for use around the tip of a finger or toe. In this embodiment, an opaque piece of tape 46 is cut into a butterfly shape. A second opaque piece of tape 48, with two openings 50 cut out to allow for the lenses 22 to pass through the openings 50, is then placed over the top surface of the lead frame 12. A transparent tape layer 52 is then placed over the top of each of the lenses 22 that protrude through the opaque tape 48.

Figure 9A:
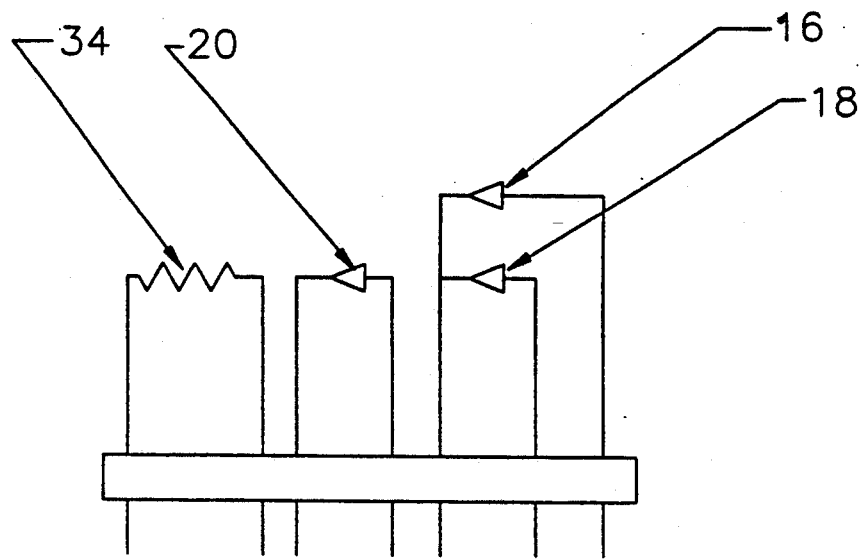
FIGS. 9(a)-9(b) are schematic views of a seven lead sensor and a six lead sensor, respectively, of the present invention.
Figure 9B:
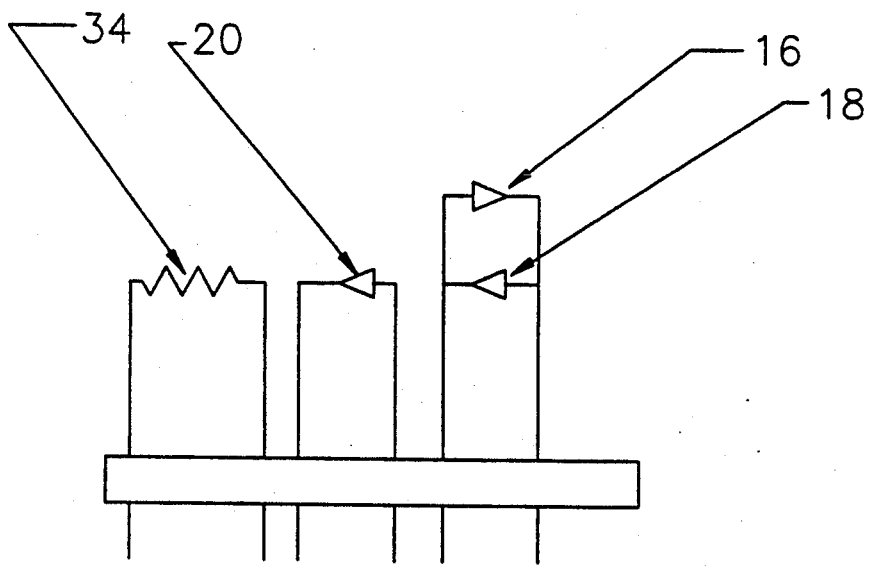

While the sensor shown in FIGS. 1-8 include seven leads, other embodiments will include only six leads. Referring to FIG. 9(a), a schematic for a seven lead version is shown in which two leads are connected to the calibration resistor 34, two leads are connected to the photodiode 20 and the other three leads are connected to the two LEDs 16,18. In the six lead embodiment shown in FIG. 9(b), two leads are also connected to the calibration code element 34 and another two are connected to the photodiode 20. The difference in the FIG. 9(b) embodiment is that only two leads are connected to the two LEDs. The selection of the particular type of lead depends on the oximetry instrument that is being used with the sensor.

Referring now to FIGS. 10(a)-10(c), the lead frame 12 can be shielded with a grounded planar shield 54 as shown in FIG. 10(a). The shield is created by covering a layer of planar shield material 56 with a plastic film insulator 58. The shield is then folded length wise in half so that the plastic film insulator 58 is completely surrounded by the layer of planar shield material 56 as shown in FIG. 10(b). The shield is shown in FIG. 10(c) with one lens mounted over the shield.

In the preferred embodiment shown in FIGS. 1-10, the sensor is shown with a flat flexible cable connector system which includes a detent or groove 15 that mates with a projection 17 in the female connector 26. As shown in FIGS. 11(a)-11(b), inside the molded female connector housing 26, a metal spring contact 60 is positioned which is designed to mate with the lead frame conductor 62 which passes through the molded connector shell 14. As shown in FIG. 11(a) the spring contact 60 will contact the lead frame conductor 62 when the two elements 14, 26 are connected.

Instead of using the connector system that utilizes the detent or groove 15 and projection 17, an alternate embodiment shown in FIG. 12 utilizes a cable 64 that is permanently attached to the sensor element. In other words, each wire will be connected to an individual lead frame trace 66 at one end of the sensor lead frame 12.

Referring to FIGS. 13(a)-13(b), another alternate embodiment is shown which utilizes a pin and socket connector system. In this embodiment, the female sockets 68 are attached to each lead frame trace 66. The female sockets 68 receive mating pins 70 that extend from the cable connector 72.

In still another embodiment of the invention shown in FIGS. 14(a)-14(b) a cantilevered "U" socket connector is utilized. In this embodiment, the ends of each lead frame trace 74 are shaped in the form of a U socket 76 which receives mating pins 78 that extend from the cable connector 80.

In the embodiment shown in FIGS. 15(a)-15(c), the lead frame 86 can be designed to be connected to the oximetry instrument at either end as it includes a connector shell 84 at each end of the lead frame 86. An interconnection cable can be permanently attached to one end of the FIG. 15(c) configuration, and either the connector on one end or the cable on the other end can be removed if not used. This lead frame can also be adapted for use with different oximetry instruments. Once the oximetry instrument is selected, the final configuration is chosen simply by cutting the extra leads.

While the foregoing invention has been described with reference to its preferred embodiments, various alterations and modifications will occur to those skilled in the art. All such variations and modifications are intended to fall within the scope of the appended claims:

What is claimed is:

1. A pulse oximetry probe for use with a pulse oximetry instrument, said probe comprising:
   a self-supporting lead frame having a plurality of electrically conductive leads, said leads having a thickness between 0.1 and 0.3 millimeters;
   at least two light sources of different wavelengths, each of said light sources being connected to at least one of said a plurality of electrically conductive leads;
   a photodetector for detecting light emitted by said light sources, said photodetector being connected to at least one of said plurality of electrically conductive leads.

2. The pulse oximetry probe of claim 1 wherein said light sources are light emitting diodes.

3. The pulse oximetry probe of claim 1 wherein said photodetector is a silicon photodiode.

4. The pulse oximetry probe of claim 1 wherein said lead frame is made of copper or a copper alloy.

5. The pulse oximetry of claim 1 wherein the lead frame is plated with gold.

6. The pulse oximetry probe of claim 1 wherein the lead frame is plated with silver.

7. The pulse oximetry probe of claim 1 wherein the lead frame is plated with palladium.

8. The pulse oximetry probe of claim 1 wherein said lead frame further comprises a dish shaped reflector for supporting said light sources or photodetector.

9. The pulse oximetry probe of claim 1 wherein said light sources are encapsulated in clear epoxy to provide mechanical integrity.

10. The pulse oximetry probe of claim 9 wherein the epoxy is formed in the shape of an optical lens to optimize the performance of the light sources.

11. The pulse oximetry probe of claim 1 wherein the lead frame further comprises a shield layer that provides additional shielding from ambient light.

12. The pulse oximetry probe of claim 1 wherein the lead frame further comprises a shield layer that provides additional shielding from electromagnetic interference.

13. The pulse oximetry probe of claim 1 wherein said lead frame is deformable plastically when applied to perfused tissue and wherein said lead frame retains the shape desired by the user.

14. The pulse oximetry probe of claim 1 further comprising a calibration element connected to at least one lead of said lead frame.

15. The pulse oximetry probe of claim 1 wherein said lead frame is permanently connected to an interconnection cable.

16. The pulse oximetry probe of claim 1 wherein the lead frame is terminated to a reusable connector element.

17. The pulse oximetry probe of claim 16, wherein the connector element is configured as the male end of a flat flexible cable (FFC) connector system.

18. The pulse oximetry probe of claim 16 wherein the connector element is configured as the female end of a pin and socket connector system.

19. The pulse oximetry probe of claim 18 wherein lead traces of the lead frame are formed to create U-shaped cantilevered socket elements.

20. The pulse oximetry probe of claim 16 wherein rigid plastic is insert molded around the connector to provide mechanical spacing and electrical insulation between conductors.

21. The pulse oximetry probe of claim 20 wherein molded rigid plastic insert also incorporates a snap detent means for connecting to a mate.

22. The pulse oximetry probe of claim 20 wherein the molded rigid plastic insert further comprises a moisture seal.

23. The pulse oximetry probe of claim 1 wherein said lead frame comprises both a reusable connector and a permanently attached interconnection cable, one of said connector or cable being removable if not required.

24. The pulse oximetry probe of claim 1 wherein the lead frame comprises at least two sets of light sources and at least two photodetectors.

25. The pulse oximetry probe of claim 1 wherein said lead frame comprises connector elements at each end of the lead frame so that the oximetry instrument can be connected to the pulse oximetry sensor at either end of the pulse oximetry sensor.

26. The pulse oximetry probe of claim 1 further comprising:
a first layer of opaque material on which said lead frame is positioned;
a second layer of opaque material positioned on a surface of said lead frame opposite the surface of said lead frame in contact with said first layer of opaque material;
at least one layer of transparent material for covering said light sources and said photodetector.

27. The pulse oximetry probe of claim 1 further comprising to make electrical contact with a spring element housed within a connector mounted on a cable to which said pulse oximetry probe is connected.

28. The pulse oximetry probe of claim 1 wherein at least one of said conductive leads is removable if said pulse oximetry probe is to be used with a oximetry instrument which does not require use of all of the leads of the probe.

29. The pulse oximetry probe of claim 1 wherein said photodetector is encapsulated in clear epoxy to provide mechanical integrity.

30. The pulse oximetry probe of claim 29 wherein said epoxy encapsulating said photodetector is tinted to provide shielding from ambient light.

* * * * *